United States Patent
Shamain et al.

(10) Patent No.: US 11,054,511 B2
(45) Date of Patent: Jul. 6, 2021

(54) PHASOR APPROACH TO SIGNAL TO NOISE RATIO MEASUREMENT EVALUATION OF PHYSIOLOGICAL SIGNALS

(71) Applicant: Nokia Technologies Oy, Espoo (FI)

(72) Inventors: Durgaprasad Shamain, San Jose, CA (US); Wuyuan Li, Chapel Hill, NC (US)

(73) Assignee: Nokia Technologies Oy, Espoo (FI)

( * ) Notice: Subject to any disclaimer, the term of this patent is extended or adjusted under 35 U.S.C. 154(b) by 366 days.

(21) Appl. No.: 15/848,421

(22) Filed: Dec. 20, 2017

(65) Prior Publication Data
US 2018/0180728 A1  Jun. 28, 2018

(30) Foreign Application Priority Data

Dec. 28, 2016  (EP) .................................... 16207032

(51) Int. Cl.
    *G01S 13/02*  (2006.01)
    *H04B 1/69*   (2011.01)
    (Continued)

(52) U.S. Cl.
    CPC ........ *G01S 13/0209* (2013.01); *A61B 5/0507* (2013.01); *A61B 5/7235* (2013.01); *A61B 5/7253* (2013.01); *G01S 7/023* (2013.01); *G01S 7/2923* (2013.01); *G01S 7/2926* (2013.01); *G01S 7/354* (2013.01); *G01S 7/414* (2013.01); *G01S 13/88* (2013.01); *H04B 1/69* (2013.01);
    (Continued)

(58) Field of Classification Search
    None
    See application file for complete search history.

(56) References Cited

U.S. PATENT DOCUMENTS 8,454,528 B2  6/2013  Yuen et al.
8,562,526 B2  10/2013  Heneghan et al.
(Continued)

FOREIGN PATENT DOCUMENTS

WO  2010/132850 A1  11/2010
WO  2011/146517 A2  11/2011

OTHER PUBLICATIONS

Tian, "An Ultra-Wide Band Radar Based Noncontact Device for Real-time Apnea Detection", Thesis, Nov. 2015, 53 pages.
(Continued)

*Primary Examiner* — Whitney Moore
(74) *Attorney, Agent, or Firm* — Mendelsohn Dunleavy, P.C.; Yuri Gruzdkov

(57) ABSTRACT

Various sensing systems may benefit from appropriate handling of signal to noise ratios. For example, detecting and measuring physiological signals may benefit from a phasor approach to signal to noise ratio measurement evaluation. A method can include obtaining a plurality of observations of a target volume. The method can also include determining a weight for each observation of the plurality of observations of the volume. The weight can be based on a change in phasor characteristics of the observation. The method can further include combining the plurality of observations based on the weight. The method can additionally include identifying a physiological signal based on the combined observations.

19 Claims, 4 Drawing Sheets

(51) Int. Cl.
*G01S 7/02* (2006.01)
*A61B 5/0507* (2021.01)
*G01S 7/292* (2006.01)
*A61B 5/00* (2006.01)
*G01S 7/41* (2006.01)
*G01S 13/88* (2006.01)
*G01S 7/35* (2006.01)
*H04B 17/391* (2015.01)
*H04B 17/336* (2015.01)
*A61B 5/024* (2006.01)
*A61B 5/08* (2006.01)

(52) U.S. Cl.
CPC .............. *A61B 5/024* (2013.01); *A61B 5/0816* (2013.01); *H04B 17/336* (2015.01); *H04B 17/391* (2015.01)

(56) References Cited

U.S. PATENT DOCUMENTS

| | | | |
|---|---|---|---|
| 2008/0074307 | A1 | 3/2008 | Boric-Lubecke et al. |
| 2008/0077015 | A1 | 3/2008 | Boric-Lubecke et al. |
| 2009/0278728 | A1 | 11/2009 | Morgan et al. |
| 2010/0152600 | A1* | 6/2010 | Droitcour ............... A61B 5/05 600/534 |
| 2011/0060215 | A1 | 3/2011 | Tupin, Jr. et al. |
| 2013/0135137 | A1 | 5/2013 | Mulder et al. |
| 2015/0363215 | A1* | 12/2015 | Versteeg ............ G06F 11/3684 703/23 |

OTHER PUBLICATIONS

Droitcour, "Non-Contact Measurement of Heart and Respiration Rates with a Single-Chip Microwave Doppler Radar", A Dissertation, Jun. 2006, 470 pages.

Kazemi et al., "Cyclostationary Approach for Heart and Respiration Rates Monitoring with Body Movement Cancellation Using Radar Doppler System", arXiv: Medical Physics, Oct. 8, 2013, pp. 1-9.

Extended European Search Report received for corresponding European Patent Application No. 16207032.0, dated Jun. 30, 2017, 8 pages.

Communication pursuant to Article 94(3) EPC for corresponding European application No. 16207032.0; dated Apr. 20, 2020 (4 pages).

* cited by examiner

PHASOR APPROACH TO SIGNAL TO NOISE RATIO MEASUREMENT EVALUATION OF PHYSIOLOGICAL SIGNALS

BACKGROUND

Field

Various sensing systems may benefit from appropriate handling of signal to noise ratios. For example, detecting and measuring physiological signals may benefit from a phasor approach to signal to noise ratio measurement evaluation.

SUMMARY

According to certain embodiments, a method can include obtaining a plurality of observations of a target volume. The method can also include determining a weight for each observation of the plurality of observations of the volume. The weight can be based on a change in phasor characteristics of the observation. The method can further include combining the plurality of observations based on the weight. The method can additionally include identifying a physiological signal based on the combined observations.

An apparatus, according to certain embodiments, can include at least one processor and at least one memory including computer program code. The at least one memory and the computer program code can be configured to, with the at least one processor, cause the apparatus at least to perform a process. The process can include obtaining a plurality of observations of a target volume. The process can also include determining a weight for each observation of the plurality of observations of the volume. The weight can be based on a change in phasor characteristics of the observation. The process can further include combining the plurality of observations based on the weight. The process can additionally include identifying a physiological signal based on the combined observations.

A computer program product, according to certain embodiments, can encode instructions for performing a process. The process can include obtaining a plurality of observations of a target volume. The process can also include determining a weight for each observation of the plurality of observations of the volume. The weight can be based on a change in phasor characteristics of the observation. The process can further include combining the plurality of observations based on the weight. The process can additionally include identifying a physiological signal based on the combined observations.

A non-transitory computer-readable medium can, in certain embodiments, be encoded with instructions that, when executed in hardware, perform a process. The process can include obtaining a plurality of observations of a target volume. The process can also include determining a weight for each observation of the plurality of observations of the volume. The weight can be based on a change in phasor characteristics of the observation. The process can further include combining the plurality of observations based on the weight. The process can additionally include identifying a physiological signal based on the combined observations.

BRIEF DESCRIPTION OF THE DRAWINGS

For proper understanding of the present disclosure, reference should be made to the accompanying drawings, wherein.

DETAILED DESCRIPTION

Figure 1:
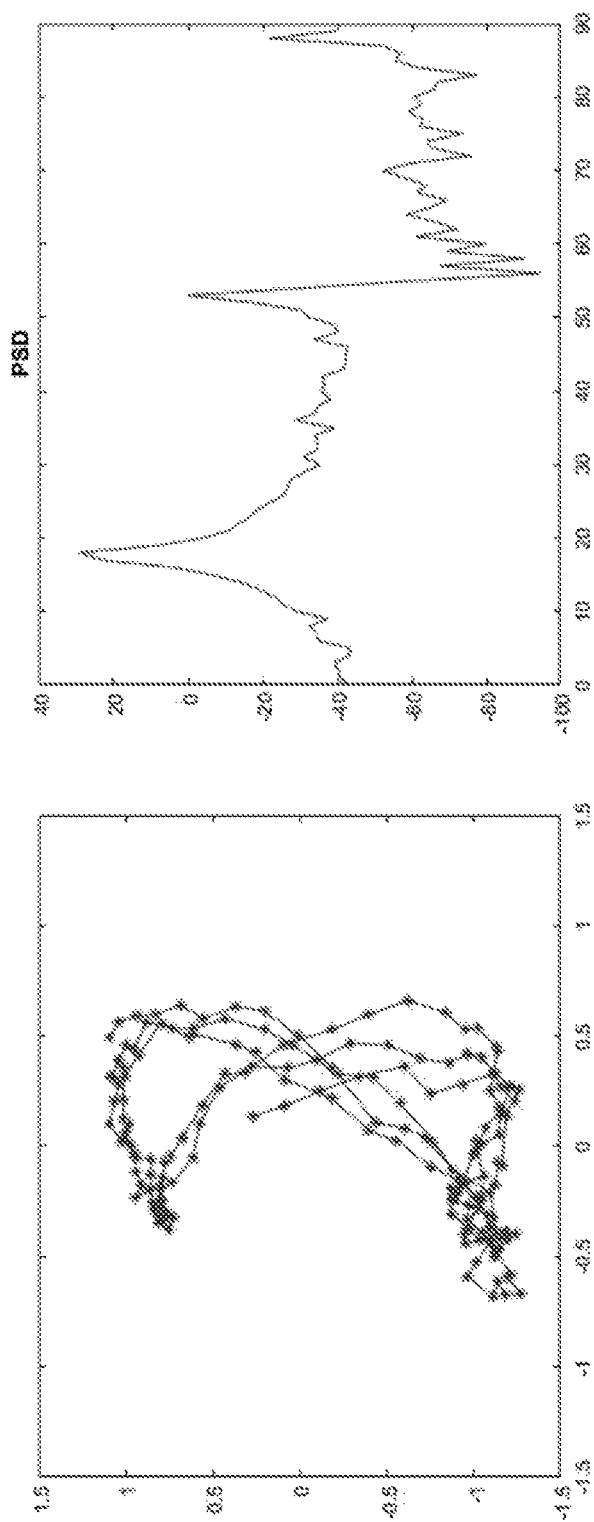
FIG. 1 illustrates a plot of observations of a small robot including an I/Q plot and PSD plot.

Combining various replicas of digitally modulated signals based on signal to noise ratio (SNR) has been studied. These digitally modulated signals include, for example, quaternary phase shift keyed (QPSK). However, the measurement of respiration and heart-beat using radar conventionally involves analog modulated signals, such as frequency modulated (FM) signals. Unlike digital modulation, analog-modulated signals do not have a very well defined signature, because there are no "0" and "1" but a continuum of values and because respiration and heart-beat are physiological signals and vary significantly from person to person. For these reasons, the traditional definition of SNR based on the signal's power-spectral density (PSD) does not extend to these analog signals.

Notwithstanding these limitations, respiration and heartbeat signals have some structure in the phasor domain that can distinguish these physiological signals from other interference. Non-contact vital sign monitoring can be performed on physiological signals such as respiration rate and heart rate. Monitoring using Doppler radar can be done using a continuous-wave (CW) Doppler radar, equipped with one receiving antenna and one transmitting antenna, single input single output (SISO). In such an approach the system observes the radio wave reflected by the object(s) in a certain area.

Accordingly, certain embodiments may enhance the detection and monitoring of analog signals, such as physiological signals, including respiration and heartbeat signals, for example. Certain embodiments may apply a signal to noise ratio (SNR) metric to combine multiple observations to enhance the robustness and reliability of the results. Furthermore, certain embodiments may apply the SNR metric to reject interference that may resemble the physiological signals.

Certain embodiments may rely on pulsed radar rather than continuous wave (CW) radar. Moreover, certain embodiments may provide a method of signal combining in the presence of interference for pulsed radar. The interference may resemble respiration and heartbeat in power spectral density (PSD) based SNR. The method of certain embodiments may identify that various replicas have specific phase relationship among them and these replicas have specific structure, such as expected arc length.

Certain embodiments may involve several possible upgrades. For example, certain embodiments may use several antennas, multiple-input multiple-output (MIMO) and apply beam-forming technique to distinguish radio waves from different direction-of-arrival (DOA). Moreover, certain embodiments may replace CW radar by ultra-wideband (UWB) radar to distinguish radio waves reflected by targets at different distances.

Such upgrades may reduce system noise, especially in complex environments like offices and bedrooms, where there are many objects beside the person(s) being monitored, and where multipath effect may exist.

While the target may be at a predetermined location or the location of the target may be estimated based on signal power, in many cases the subject being monitored may not have a constant position. Thus, estimation of target location may be important. Also, for UWB radar or MIMO radar, target movement information may be contained in a certain area instead of a single point. For example, breathing information may be contained in almost the entire torso, and a heartbeat signal may be observable almost over the entire chest.

Certain embodiments provide a way to combine signals observed at a range of distance bins or direction-of-arrival (DOA) groups. This combination can increase the signal power, and make the system more robust. For example, such combination may help against ambient noise caused by a vibrating fan or similar moving objects that may exist in the environment.

The basic idea behind Doppler radar is that the radar transmits an electromagnetic wave, listens to the signal reflected from the target (echo), and determines information of the target including distance, moving speed, and so on. There are several kinds of Doppler radar: CW, UWB, and frequency modulated continuous wave (FMCW). CW radar keeps transmitting a narrowband continuous wave and listening to the echo all the time. UWB radar transmits a very short pulse every now and then and listens to the echo for each pulse. FMCW transmits a continuous wave whose carrier frequency shifts following some patterns. These descriptions may be understood as high-level summaries of typical characteristics of examples of Doppler radar, which should not be taken as limiting.

Each radar may have its own advantages and disadvantages. For example, CW radar is simple and sensitive, yet vulnerable to environmental noise and cannot do multi-target monitoring. UWB radar is probably the least sensitive due to its bandwidth, yet it is robust against environmental noise and can do multi-target monitoring. FMCW radar can be viewed as a compromise between CW and UWB, it has some ability to do multi-target monitoring, and is still relatively sensitive.

However, unless the subject and the radar are in a clean environment, wave reflection from the environment may interfere with the radar system's observation. A MIMO system has the ability of distinguishing signals coming from different directions of arrival (DOA), and UWB radar has the ability of distinguish signals reflected from different distances.

In a MIMO system, observing signals from certain directions can be done using MIMO beam-forming or DOA estimation. In UWB radar, monitoring a target at certain distance can be equivalent to range bin selection.

The human chest can be viewed as a relatively large structure. For example, chest wall movement information can be contained at a range of angles and in a range of bins. For example, a person to be observed may have a torso about 0.5 meters wide and 0.5 meters high. An UWB radar like XeThru available from Novelda AS of Norway, may have bins that sample at about 1 cm increment. Thus, more than 50 bins may contain information about respiration and heartbeat. Because the torso movement caused by respiration and heartbeat may be mostly or roughly synchronous, the same movement can be observable over these bins.

When a periodic subtle movement like a breathing pattern is being observed, the received signal on a radar system's in-phase and quadrature channel (I/Q channel) can form an arc of a circle, with a center phase determined by the distance between radar and subject. As respiration movement typically has the amplitude of b=0.5 mm or less, the arc length of the I/Q plot can be $$\frac{8\pi b}{\lambda},$$

which may be quite small. In this equation, $\lambda$ refers to the wavelength of the electromagnetic wave, which equals the speed of light in air, c, divided by the center frequency, f, of the wave, such that $$\lambda = \frac{c}{f}.$$

Since different UWB bins are observing the part of subject on different distances, the center phase of signals on different bins can be aligned. Then, the aligned signals from the observations can be summed using, a combining function, such as the maximum-ratio-combining (MRC) based on their SNR—signal power/arc fitting error.

Phase shift can be calculated based on wavelength and distance. For example, when using UWB radar, bin 1 and bin 2 may be observing distances d1 and d2, respectively. Because the wave travels to the target and gets reflected, the total traveling distance of these two bins can be 2*d1 and 2*d2, respectively. The phase difference in radians between these two bins is then $$\frac{2(d2-d1)}{\lambda}2\pi \text{ or } \frac{4\pi(d2-d1)}{\lambda}.$$

This can be the equation for a monostatic embodiment, but in a bistatic embodiment, the total traveling distance may be different from this example, as the receiver may not be collocated with the transmitter.

For other subjects like electrical appliances and moving curtains, the observation will be very different from the arc of a circle with a small arc length, which is found across multiple bins. For example, the I/Q plot of unwanted signals is unlikely to be an arc with low SNR, the movement on nearby bins is usually not synchronous due to object size or complex movement pattern; and the movement amplitude may be much larger than respiration signal, meaning the arc can be too long. These three characteristics can be used to determine if an object is a static person or noisy ambient movement.

Obtaining observations of a target volume as referred to herein may include transmitting radar pulses and receiving reflections of those radar pulses within predetermined windows. For example, a UWB radar can be used to obtain observations of a target volume.

Determining weights for observations as referred to herein may include calculating a value to be applied to the observation so that the observation can be effectively combined with other observations. The weight can be based on a change in phasor characteristics of the observation. For example, the weight of observations can be determined based on fitting a phasor distribution of the observations to an arc. Both the radius of the resulting arc and the arc-fitting error can be taken into account when weighting the observations. The weighting can also take into account whether a signal being sought is a heartbeat, a respiratory rate, or some other signal. Weighting can also be used to normalize the observations.

Combining observations as referred to herein may include associating the observations based on the weight assigned to each observation. Thus, the observations can be combined with one another after being processed. The processing can also include applying a phase offset to one or more of the observations.

Identifying physiological signals as used herein may include determining that a signal found in the combined observations is a physiological signal, such as a respiratory or vascular signal. The identification can involve a comparison to a threshold, such that if a signal being evaluated has at least some minimum similarities to a physiological signal it is determined to be a physiological signal. More particularly, the identifying can involve distinguishing a heartbeat signal from a respiratory signal. For example, in certain cases a respiratory signal may first be identified and then the respiratory signal may be filtered from the overall signal and then a heartbeat signal may be identified from the filtered signal. This may be done in a target volume that is associated with both the heartbeat signal and the respiratory signal.

The identification can be based on the length of the arc to which the observations are fit. Also, the identification can be based on the spatial distribution of the physiological signal. For example, an excessively long arc or an excessively small spatial distribution may suggest that the signal is an environmental or other noise signal.

FIG. 1 illustrates a plot of observations of a small robot including an I/Q plot and PSD plot. As can be seen from FIG. 1, the trajectory of the small robot observations has the shape of an "8" instead of the shape of an arc. Thus, the arc fitting error is large and SNR is very small. Additionally, because the object is much smaller than the torso of a person, the detected movement exists only in a small range of bins.

Figure 2:
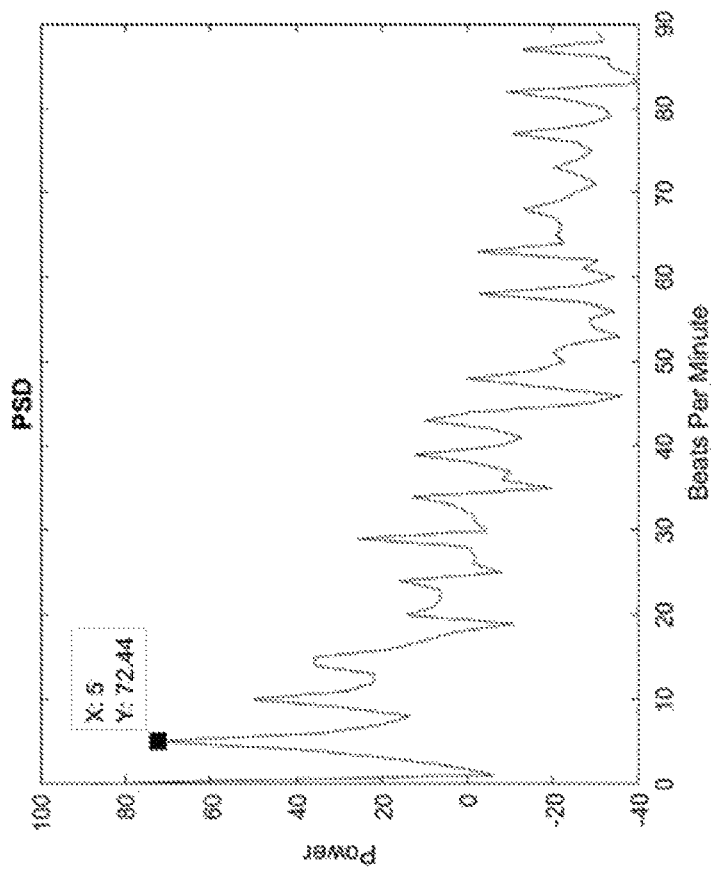
FIG. 2 illustrates a plot of observations of a tower fan, including an I/Q plot and PSD plot.
Figure 2:
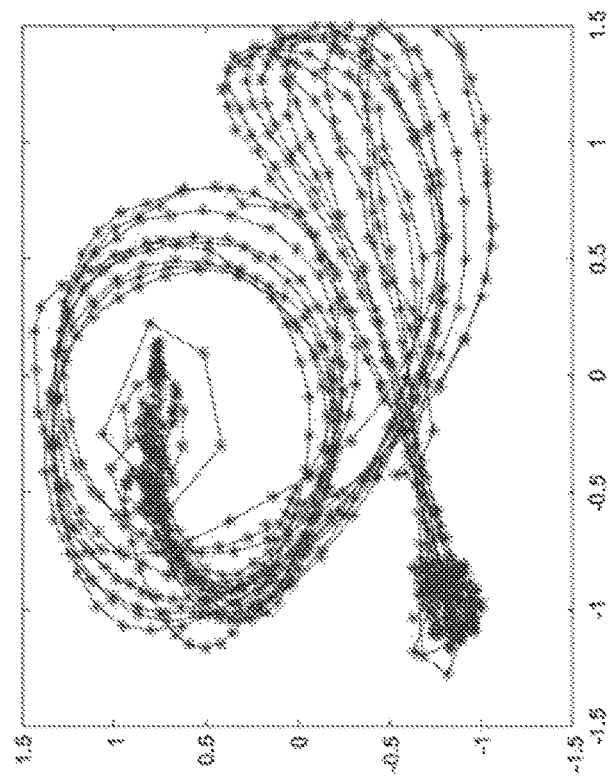

FIG. 2 illustrates a plot of observations of a tower fan, including an I/Q plot and PSD plot. The tower fan may have two sources of motion: rotation of the fan blades and rotation of the tower itself about its axis. Once again, as can be seen from FIG. 2, the trajectory of the observations is quite different from an arc. Thus, the arc fitting error is large and SNR is very small. Additionally, the movement is much larger than an expected respiration pattern, such that even when the detected movement is fit to an arc, the arc length is too long.

Figure 3:
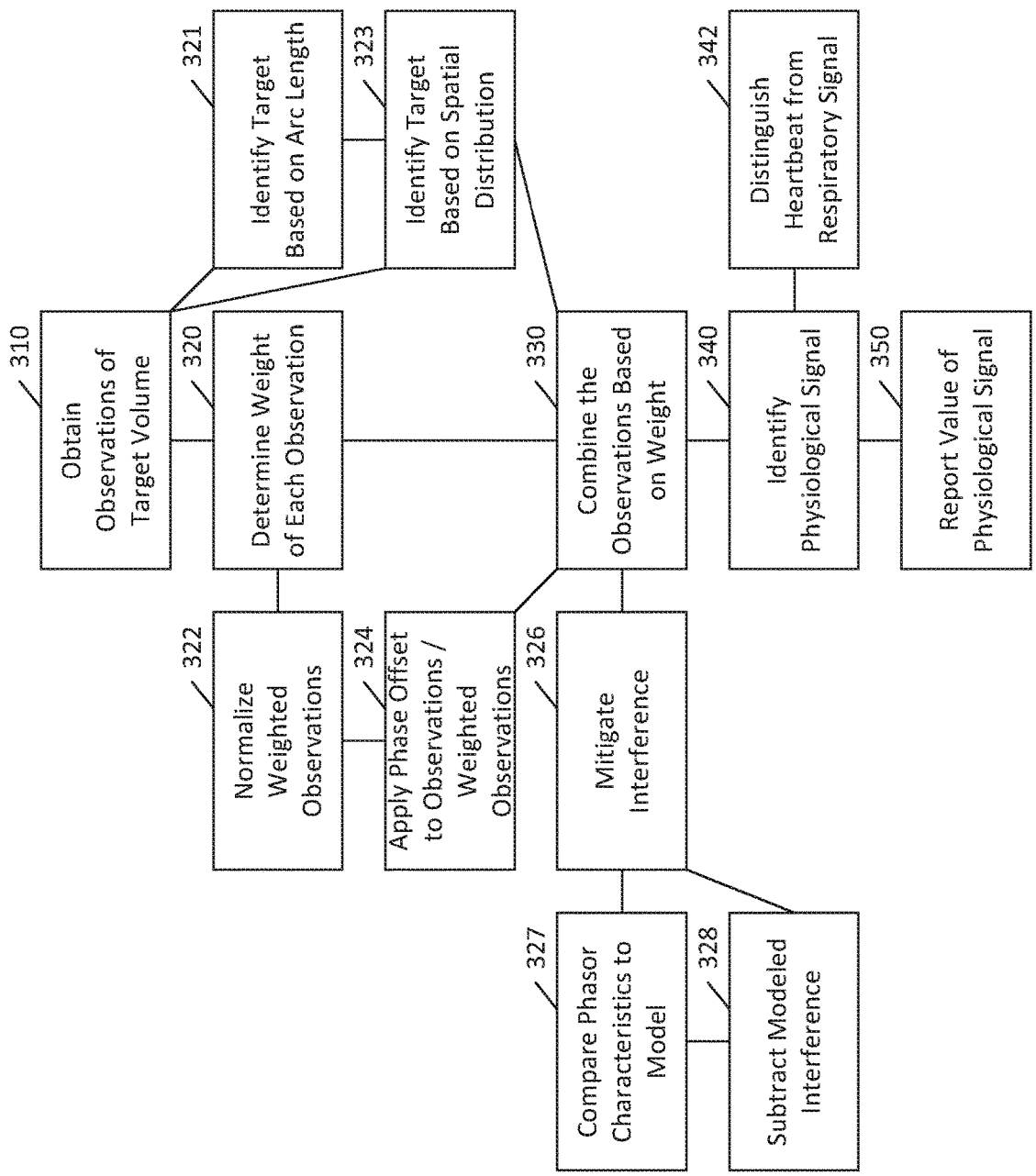
FIG. 3 illustrates a method according to certain embodiments.

FIG. 3 illustrates a method according to certain embodiments. As shown in FIG. 3, a method can include, at 310, obtaining a plurality of observations of a target volume. These observations can be obtained using a radar system, such as a UWB radar system. The observations can be multiple measurements of a single sub-volume of the volume over a length of time. The observations can also include similar multiple measurements over other sub-volumes of the volume over the same length of time. Thus, for example, a single observation may correspond to a multiple measurements.

The method can also include, at 320, determining a weight for each observation of the plurality of observations of the volume. The weight can be based on a change in phasor characteristics of the observation. The weight can be determined based on fitting a phasor distribution of the observations to an arc. For example, the weight can be determined based on a radius of the arc. The weight can also or additionally be determined based on arc-fitting error of the arc. The weighting can take into consideration whether a desired signal is respiratory or cardiovascular. In certain embodiments, both kinds of signals can be separately detected for a particular living organism, such as a human.

The method can also include, at 321, identifying a target from the plurality of observations based on the length of the arc. For example, the target can be identified as a human if the length of the arc corresponds to a range of arc lengths associated with human respiration or cardiovascular activity. Alternatively, the target can be rejected as human if the length of the arc is too long. Similarly, the signal can be identified or rejected as a physiological signal based on these same criteria.

The method can further include, at 323, identifying a target from the plurality of observations based on the spatial distribution of the physiological signal. For example, the target can be identified as human if a signal exists approximately in synchronization across a volume corresponding to the human torso in the case of a respiratory signal or a human chest in the case of a cardiovascular signal. As human sizes may vary, a range of volumes may be accepted for example using a statistical distribution of human torso or chest sizes and selecting volumes falling within three or six standard deviations the average torso or chest size. If the system is trying to identify a particular person, the range could be selected with greater specificity.

The SNR measurement using the phasor approach may require estimating the parameters of the circle or arc that would best fit a set of observation data-points and then calculating the errors for these points to the fitted arc.

Having a strong frequency component in the respiration band (for example, 0.1 Hz to 0.5 Hz) of the PSD could be due to some other source. One way to tell if this belongs to respiration is if over the period of measurement for example, a minute, the points on the phasor space oscillate between the two ends of the associated arc for the same measurement period.

Similarly, a strong frequency component in the pulse band (for example, 20 bpm to 220 bpm) may be due to some other source. As with a respiration signal, a heartbeat signal can be evaluated over time to see if the points on the phasor space oscillate between the two ends of the associated arc for the same measurement period.

The method can further include, at 330, combining the plurality of observations based on the weight. At 322, the method can also include normalizing the weighted observations prior to combining the weighted observations. The method can also include, at 324, applying a phase offset to the observations or weighted observations prior to combining the weighted observations.

The method can further include, at 326, mitigating interference in the observation prior to combining the weighted observations. For example, interference can be identified as corresponding to a simple mechanical source of motion, such as a fan or the like. The mitigating interference can include, at 327, comparing the phasor characteristics of the observation to a model of interference and, at 328, subtracting interference when the modeled interference is determined to be present. The model of interference may be, for example, a shape based on a previously identified source of interference, such as a small robot or fan.

The method can additionally include, at 340, identifying a physiological signal based on the combined observations. The physiological signal can be a heartbeat or respiration signal, for example. The identifying can include simply identifying presence or absence of the signal, or identifying a particular value of the signal. The identifying can include, at 342, distinguishing a heartbeat signal from a respiratory signal in an area associated with both the heartbeat signal and the respiratory signal. In certain embodiments, an identified respiration signal can be subtracted as though it were noise and the resulting signal can then be evaluated for a heartbeat signal.

The method can also include, at 350, reporting a value of the physiological signal. The reporting the value can involve outputting the value electronically to a local or remote device or outputting the value visually to a user of a local or remote device.

Figure 4:
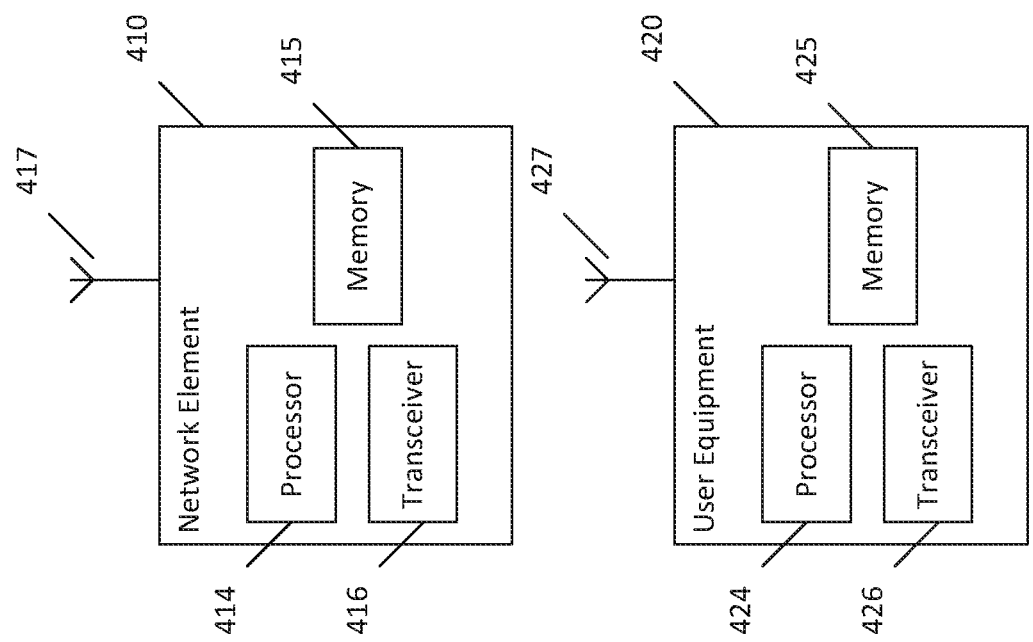
FIG. 4 illustrates a system according to certain embodiments.

FIG. 4 illustrates a system according to certain embodiments of the present disclosure. It should be understood that each block of the flowchart of FIG. 3 may be implemented by various means or their combinations, such as hardware, software, firmware, one or more processors and/or circuitry. In one embodiment, a system may include several devices, such as, for example, network element 410 and user equipment (UE) or user device 420. The system may include more than one UE 420 and more than one network element 410, although only one of each is shown for the purposes of illustration. A network element can be a server, remote user terminal, or other device. The UE 420 can be a local device. The two devices 410 and 420 can be configured to work together, for example to perform telemedicine or other services.

Each of these devices may include at least one processor or control unit or module, respectively indicated as 414 and 424. At least one memory may be provided in each device, and indicated as 415 and 425, respectively. The memory may include computer program instructions or computer code contained therein, for example for carrying out the embodiments described above. One or more transceiver 416 and 426 may be provided, and each device may also include an antenna, respectively illustrated as 417 and 427. Although only one antenna each is shown, many antennas and multiple antenna elements may be provided to each of the devices. For example, the UE 420 may be equipped with a MIMO configuration of antennas to provide directional sensing. The transceiver 426 of the UE may include circuitry configured to operate as a UWB radar in combination with antenna 427. Other configurations of these devices, for example, may be provided. For example, network element 410 and UE 420 may be additionally configured for wired communication, in addition to wireless communication, and in such a case antennas 417 and 427 may illustrate any form of communication hardware, without being limited to merely an antenna.

Transceivers 416 and 426 may each, independently, be a transmitter, a receiver, or both a transmitter and a receiver, or a unit or device that may be configured both for transmission and reception. The transmitter and/or receiver (as far as radio parts are concerned) may also be implemented as a remote radio head which is not located in the device itself, but in a mast or peripheral wand, for example. One or more functionalities may also be implemented as a virtual application that is provided as software that can run on a server.

A user device or user equipment 420 may be a mobile station (MS) such as a mobile phone or smart phone or multimedia device, a computer, such as a tablet, provided with wireless communication capabilities, personal data or digital assistant (PDA) provided with wireless communication capabilities, vehicle, portable media player, digital camera, pocket video camera, navigation unit provided with wireless communication capabilities or any combinations thereof. The user device or user equipment 420 may be a sensor or smart meter, or other device that may usually be configured for a single location.

In an exemplifying embodiment, an apparatus, such as a node or user device, may include means for carrying out embodiments described above in relation to FIG. 3.

Processors 414 and 424 may be embodied by any computational or data processing device, such as a central processing unit (CPU), digital signal processor (DSP), application specific integrated circuit (ASIC), programmable logic devices (PLDs), field programmable gate arrays (FPGAs), digitally enhanced circuits, or comparable device or a combination thereof. The processors may be implemented as a single controller, or a plurality of controllers or processors. Additionally, the processors may be implemented as a pool of processors in a local configuration, in a cloud configuration, or in a combination thereof. The term circuitry may refer to one or more electric or electronic circuits. The term processor may refer to circuitry, such as logic circuitry, that responds to and processes instructions that drive a computer.

For firmware or software, the implementation may include modules or units of at least one chip set (e.g., procedures, functions, and so on). Memories 415 and 425 may independently be any suitable storage device, such as a non-transitory computer-readable medium. A hard disk drive (HDD), random access memory (RAM), flash memory, or other suitable memory may be used. The memories may be combined on a single integrated circuit as the processor, or may be separate therefrom. Furthermore, the computer program instructions may be stored in the memory and which may be processed by the processors can be any suitable form of computer program code, for example, a compiled or interpreted computer program written in any suitable programming language. The memory or data storage entity is typically internal but may also be external or a combination thereof, such as in the case when additional memory capacity is obtained from a service provider. The memory may be fixed or removable.

The memory and the computer program instructions may be configured, with the processor for the particular device, to cause a hardware apparatus such as network element 410 and/or UE 420, to perform any of the processes described above (see, for example, FIG. 3). Therefore, in certain embodiments, a non-transitory computer-readable medium may be encoded with computer instructions or one or more computer program (such as added or updated software routine, applet or macro) that, when executed in hardware, may perform a process such as one of the processes described herein. Computer programs may be coded by a programming language, which may be a high-level programming language, such as objective-C, C, C++, C#, Java, etc., or a low-level programming language, such as a machine language, or assembler. Alternatively, certain embodiments of the present disclosure may be performed entirely in hardware.

Furthermore, although FIG. 4 illustrates a system including a network element 410 and a UE 420, embodiments of the present disclosure may be applicable to other configurations, and configurations involving additional elements, as illustrated and discussed herein. For example, multiple user equipment devices and multiple network elements may be present, or other nodes providing similar functionality.

Additionally different radar types are permitted, such as both monostatic and bistatic radar systems. In a monostatic radar system both the transmitter and receiver may be collocated and may optionally use the same antenna for both transmitting and receiving. In a bistatic system the receiver may be spatially separated from the transmitter. Various embodiments can be applied to each of these example radar types.

Certain embodiments may have various benefits and/or advantages. For example, certain embodiments provide for the simultaneous use of SNR measured in phasor space for two things: to identify suitable spatial bins for combination, and determining the weights used for each bin in the combination function. More generally, certain embodiments can provide for the combination of different bins in order to achieve better signal quality.

One having ordinary skill in the art will readily understand that the present disclosure as discussed above may be practiced with steps in a different order, and/or with hardware elements in configurations which are different than those which are disclosed. Therefore, although the present disclosure has been described based upon these preferred embodiments, it would be apparent to those of skill in the art that certain modifications, variations, and alternative constructions would be apparent, while remaining within the spirit and scope of the present disclosure.

We claim:

1. A method, comprising:
    obtaining a plurality of observations of a target volume by operating a transceiver to transmit radar pulses and receive reflections of the radar pulses within predetermined windows, the observations being directed for processing to a data processing device, said processing including:
        determining a weight for each observation of the plurality of observations of the target volume, wherein the weight is based on phasor characteristics of the observation;
        combining the plurality of observations based on the weight, said combining including combining at least some of the observations corresponding to a range of distance bins;
        mitigating interference in the observation prior to combining the weighted observations; and
        identifying a physiological signal based on the combined observations.

2. The method of claim 1, wherein the identifying comprises distinguishing a heartbeat signal from a respiratory signal in an area associated with both the heartbeat signal and the respiratory signal.

3. The method of claim 1, wherein the weight is determined based on fitting a phasor distribution of the observations to an arc.

4. The method of claim 3, wherein the weight is determined based on a radius of the arc.

5. The method of claim 3, wherein the weight is determined based on arc-fitting error of the arc.

6. The method of claim 3, wherein the weighting takes into consideration whether a desired signal is respiratory or cardiovascular.

7. The method of claim 3, further comprising:
    identifying a target from the plurality of observations based on a length of the arc.

8. The method of claim 1, further comprising:
    identifying a target from the plurality of observations based on a spatial distribution of the physiological signal.

9. The method of claim 1, further comprising:
    normalizing the weighted observations prior to combining the weighted observations.

10. The method of claim 1, further comprising:
    applying a phase offset to the observations or weighted observations prior to combining the weighted observations.

11. The method of claim 1, wherein the mitigating interference comprises comparing the phasor characteristics of the observation to a model of interference and subtracting interference when the modeled interference is determined to be present.

12. The method of claim 11, wherein the model of interference is a shape based on a previously identified source of interference.

13. An apparatus, comprising:
    a transceiver configured to transmit radar pulses and receive reflections of the radar pulses within predetermined windows, said reflections being detected by the transceiver to obtain a plurality of observations of a target volume, at least some of said observations corresponding to a range of distance bins;
    at least one processor; and
    at least one memory including computer program code,
    wherein the at least one memory and the computer program code are configured to, with the at least one processor, cause the apparatus at least to:
    determine a weight for each observation of the plurality of observations of the target volume, wherein the weight is based on phasor characteristics of the observation;
    combine the plurality of observations based on the weight;
    mitigate interference in the observation prior to combining the weighted observations; and
    identify a physiological signal based on the combined observations.

14. The apparatus of claim 13, wherein the at least one memory and the computer program code are configured to, with the at least one processor, cause the apparatus at least to distinguish a heartbeat signal from a respiratory signal in an area associated with both the heartbeat signal and the respiratory signal.

15. The apparatus of claim 13, wherein the weight is determined based on fitting a phasor distribution of the observations to an arc.

16. The apparatus of claim 15, wherein the weight is determined based on one or both of:
    a radius of the arc; and
    arc-fitting error of the arc.

17. The apparatus of claim 15, wherein the weight takes into consideration whether a desired signal is respiratory or cardiovascular.

18. The apparatus of claim 15, wherein the at least one memory and the computer program code are configured to, with the at least one processor, cause the apparatus at least to identify a target from the plurality of observations based on a length of the arc.

19. The apparatus of claim 13, wherein the at least one memory and the computer program code are configured to, with the at least one processor, cause the apparatus at least to identify a target from the plurality of observations based on a spatial distribution of the physiological signal.

* * * * *